United States Patent
Kozian et al.

(10) Patent No.: US 7,262,273 B2
(45) Date of Patent: Aug. 28, 2007

(54) ASSOCIATION OF EDG5 POLYMORPHISM V286A WITH TYPE II DIABETES MELLITUS AND VENOUS THROMBOSIS/PULMONARY EMBOLISM AND THE USE THEREOF

(75) Inventors: Detlef Kozian, Hattersheim (DE); Evi Kostenis, Grebenau (DE); Karl-Ernst Siegler, Ludwigshafen (DE); Martina Jacobs, Mannheim (DE); Jean-Francois Deleuze, Combs la Ville (FR); Sylvain Ricard, Paris (FR); Sandrine Mace, Jouy-en-Josas (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 477 days.

(21) Appl. No.: 10/393,870

(22) Filed: Mar. 21, 2003

(65) Prior Publication Data

US 2003/0219808 A1    Nov. 27, 2003

Related U.S. Application Data

(60) Provisional application No. 60/402,305, filed on Aug. 9, 2002.

(30) Foreign Application Priority Data

Apr. 9, 2002    (EP)    .................................. 02007879

(51) Int. Cl.
  *C07K 1/00*    (2006.01)
  *G01N 33/53*   (2006.01)

(52) U.S. Cl. ........................................ 530/350; 435/7.1

(58) Field of Classification Search ..................... None
See application file for complete search history.

(56) References Cited

FOREIGN PATENT DOCUMENTS

WO    WO99/54351    10/1999

OTHER PUBLICATIONS

Kupperman et al., Accession No. Q9l8K8, 2006.*
Busch C.P. et al., Genetic Determinants Of Type 2 Diabestes Mellitus, Clin. Genet, (2001), vol. 60, pp. 243-254.
Franco Rendrik F. et al., Genetic Risk Factors Of Venous Thrombosis, Human Genetics, (2001), vol. 109, pp. 369-384.
MacLennan A.J. et al., Edg5, A Human Homolog Of Rat H218 That Is A Functional Receptor For Lysosphingolipids, Database Accession No. AF034780, XP002227241 Abstract.
MacLennan A. John et al., Cloning And Characterization Of A Putative G-Protein Coupled Receptor Potentially Involved in Development, Molecular and Cellular Neurosciences, (1994), vol. 5, No. 5, pp. 210-219.
Sesti Giorgio, Insulin Receptor Substrate Polymorphisms And Tye 2 Diabetes Mellitus, Pharmacogenomics, (2000(, vol. 1, No. 3, pp. 343-357.

* cited by examiner

*Primary Examiner*—G. R. Ewoldt
*Assistant Examiner*—Amy Juedes
(74) *Attorney, Agent, or Firm*—Karen I. Krupen

(57) ABSTRACT

The present invention relates to a method of identifying an increase in risk for type II Diabetes mellitus, venous thrombosis, or pulmonary embolism in a subject, wherein the presence of an amino acid exchange at position 286 from valine (Val) to alanine (Ala) in the EDG5 protein in a biological sample taken from the subject.

1 Claim, No Drawings

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: Oligonucleotide

<400> SEQUENCE: 1
tccactgtcc tgcctctcta c                                              21

<210> SEQ ID NO 2
<211> LENGTH: 20
<212> TYPE: DNA
<213> ORGANISM: Artificial
<220> FEATURE:
<223> OTHER INFORMATION: Oligonucleotide

<400> SEQUENCE: 2
tctccatgaa cccctctgcc                                                20

<210> SEQ ID NO 3
<211> LENGTH: 353
<212> TYPE: PRT
<213> ORGANISM: Homo sapiens

<400> SEQUENCE: 3

Met Gly Ser Leu Tyr Ser Glu Tyr Leu Asn Pro Asn Lys Val Gln Glu
1               5                   10                  15

His Tyr Asn Tyr Thr Lys Glu Thr Leu Glu Thr Gln Glu Thr Thr Ser
            20                  25                  30

Arg Gln Val Ala Ser Ala Phe Ile Val Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Ser Val
                85                  90                  95

Thr Leu Arg Leu Thr Pro Val Gln Trp Phe Ala Arg Glu Gly Ser Ala
            100                 105                 110

Ser Ile Thr Leu Ser Ala Ser Val Phe Ser Leu Leu Ala Ile Ala Ile
        115                 120                 125

Glu Arg His Val Ala Ile Ala Lys Val Lys Leu Tyr Gly Ser Asp Lys
    130                 135                 140

Ser Cys Arg Met Leu Leu Leu Ile Gly Ala Ser Trp Leu Ile Ser Leu
145                 150                 155                 160

Val Leu Gly Gly Leu Pro Ile Leu Gly Trp Asn Cys Leu Gly His Leu
                165                 170                 175

Glu Ala Cys Ser Thr Val Leu Pro Leu Tyr Ala Lys His Tyr Val Leu
```

180             185             190
Cys Val Val Thr Ile Phe Ser Ile Ile Leu Leu Ala Ile Val Ala Leu
        195                 200                 205
Tyr Val Arg Ile Tyr Cys Val Val Arg Ser Ser His Ala Asp Met Ala
    210                 215                 220
Ala Pro Gln Thr Leu Ala Leu Leu Lys Thr Val Thr Ile Val Leu Gly
225                 230                 235                 240
Val Phe Ile Val Cys Trp Leu Pro Ala Phe Ser Ile Leu Leu Leu Asp
                245                 250                 255
Tyr Ala Cys Pro Val His Ser Cys Pro Ile Leu Tyr Lys Ala His Tyr
            260                 265                 270
Phe Phe Ala Val Ser Thr Leu Asn Ser Leu Leu Asn Pro Val Ile Tyr
            275                 280                 285
Thr Trp Arg Ser Arg Asp Leu Arg Arg Glu Val Leu Arg Pro Leu Gln
        290                 295                 300
Cys Trp Arg Pro Gly Val Gly Val Gln Gly Arg Arg Val Gly Thr
305                 310                 315                 320
Pro Gly His His Leu Leu Pro Leu Arg Ser Ser Ser Leu Glu Arg
                325                 330                 335
Gly Met His Met Pro Thr Ser Pro Thr Phe Leu Glu Gly Asn Thr Val
            340                 345                 350
Val

<210> SEQ ID NO 4
<211> LENGTH: 1062
<212> TYPE: DNA
<213> ORGANISM: Homo sapiens

<400> SEQUENCE: 4

| | | | | | |
|---|---|---|---|---|---|
| atgggcagct | tgtactcgga | gtacctgaac | cccaacaagg | tccaggaaca | ctataattat | 60 |
| accaaggaga | cgctggaaac | gcaggagacg | acctcccgcc | aggtggcctc | ggccttcatc | 120 |
| gtcatcctct | gttgcgccat | tgtggtggaa | aaccttctgg | tgctcattgc | ggtggcccga | 180 |
| aacagcaagt | tccactcggc | aatgtacctg | tttctgggca | acctggccgc | ctccgatcta | 240 |
| ctggcaggcg | tggccttcgt | agccaatacc | ttgctctctg | gctctgtcac | gctgaggctg | 300 |
| acgcctgtgc | agtggtttgc | ccgggagggc | tctgcctcca | tcacgctctc | ggcctctgtc | 360 |
| ttcagcctcc | tggccatcgc | cattgagcgc | cacgtggcca | ttgccaaggt | caagctgtat | 420 |
| ggcagcgaca | gagctgccg | catgcttctg | ctcatcgggg | cctcgtggct | catctcgctg | 480 |
| gtcctcggtg | gcctgcccat | ccttggctgg | aactgcctgg | ccacctcga | ggcctgctcc | 540 |
| actgtcctgc | ctctctacgc | caagcattat | gtgctgtgcg | tggtgaccat | cttctccatc | 600 |
| atcctgttgg | ccatcgtggc | cctgtacgtg | cgcatctact | gcgtggtccg | ctcaagccac | 660 |
| gctgacatgg | ccgccccgca | gacgctagcc | ctgctcaaga | cggtcaccat | cgtgctaggc | 720 |
| gtctttatcg | tctgctggct | gcccgccttc | agcatcctcc | ttctggacta | tgcctgtccc | 780 |
| gtccactcct | gcccgatcct | ctacaaagcc | cactactttt | tcgccgtctc | caccctgaat | 840 |
| tccctgctca | accccgtcat | ctacacgtgg | cgcagccggg | acctgcggcg | ggaggtgctt | 900 |
| cggccgctgc | agtgctggcg | gccggggtg | ggggtgcaag | gacggaggcg | ggtcgggacc | 960 |
| ccgggccacc | acctcctgcc | actccgcagc | tccagctccc | tggagagggg | catgcacatg | 1020 |
| cccacgtcac | ccacgtttct | ggagggcaac | acggtggtct | ga | | 1062 |

ASSOCIATION OF EDG5 POLYMORPHISM V286A WITH TYPE II DIABETES MELLITUS AND VENOUS THROMBOSIS/PULMONARY EMBOLISM AND THE USE THEREOF

PRIORITY CLAIM

This application claims priority under 35 U.S.C. 119 from U.S. Ser. No. 60/402,305 filed on Aug. 9, 2002 and European Patent Application No. 02007879.6 filed Apr. 9, 2002, wherein said applications are hereby incorporated by reference herein in their entireties.

FIELD OF THE INVENTION

The present invention relates generally to a method of identifying an increase in risk for type II Diabetes mellitus venous thrombosis, pulmonary embolism, or a combination thereof.

BACKGROUND OF THE INVENTION

Endothelial differentiation gene (EDG) receptors are a new family of eight G protein-coupled receptors for the lysophospholipids lysophosphatitic acid and sphingosine-1-phosphate. The lysosphingolipid sphingosine 1-phosphate (S1P) regulates cell proliferation, apoptosis, motility, and neurite retraction (Pyne and Pyne, (2000) Biochem J 349: 385-402; MacLennan et al., (2001), J. of Neurosci. 14: 203-209). Its actions may be both intracellular as a second messenger and extracellular as a receptor ligand. S1P and the structurally related lysolipid mediator lysophosphatidic acid (LPA) signal through a set of G protein-coupled receptors known as EDG receptors. EDG5 (endothelial differentiation gene 5; also termed AGR16/H218) is a functional receptor for S1P. The size of the EDG5 protein is 353 amino acids and the EDG5 gene is located on chromosome 19p13.2.

Mammalian EDG-5 Receptor homologs are described in WO 99/33972.

Developmental studies in Zebrafish have indicated that S1P signaling via the EDG5 like receptor Miles Apart is essential for heart development. The presumed function of the EDG5 homologue in Zebrafish development and its expression in the heart suggests that it may play a critical role in the development and/or function of the cardiovascular system (Kupperman et al., (2000), Nature 406: 192-195).

In order to analyze potential effects of EDG5 polymorphisms in humans, the V286A polymorphism (amino acid exchange valine to alanine at position 286 of the EDG5 protein) of the EDG5 protein was studied in a clinical patient cohort enriched for cardiovascular outcomes. So far, no data was available about the clinical effects of EDG5 variants in humans. (NCBI accession number for EDG5 protein sequence: NP_004221 and NCBI accession number for EDG5 nucleotide sequence: AF034780).

The citation of any reference herein should not be construed as an admission that such reference is available as "Prior Art" to the instant application.

SUMMARY OF THE INVENTION

Broadly, the present invention extends to a method for identifying an increase in risk for type II diabetes mellitus, venous thrombosis, pulmonary embolism, or a combination thereof in a subject, comprising the steps of:
  (a) removing a biological sample from the subject that comprises an EDG5 protein; and
  (b) determining whether the amino acid residue at position 286 of the EDG5 protein from the biological sample is Alanine.

The present invention further relates to a method for identifying an increase in risk for type II Diabetes mellitus, venous thrombosis, or pulmonary embolism in a subject, comprising the steps of:
  (a) removing a biological sample from the subject that comprises a nucleic acid sequence that encodes EDG5 protein; and
  (b) determining whether the nucleic acid sequence encodes an EDG5 protein comprising an alanine residue at position 286.

In a method of the present invention, the biological sample is tissue of any type, e.g. soft tissue, bone, cartilage, etc. A biological sample can also be a bodily fluid such as blood, semen, mucus, fecal material, lymph, saliva, etc.

In addition, the present invention extends to a method for selecting patients who will respond a pharmaceutical for treating type II Diabetes mellitus, venous thrombosis, or pulmonary embolism. Such a method comprises the steps of:
  (a) removing a biological sample from the subject that comprises an EDG5 protein; and
  (b) determining whether the amino acid sequence of the EDG5 protein has an alanine residue at position 286.

Moreover, the present invention extends to a test kit for determining whether the amino acid sequence of an EDG5 protein in a biological sample taken from a subject has an alanine at position 286. Such a test kit of the present invention can be amino acid based, i.e., to evaluate the amino acid sequence of the EDG5 protein from the test sample. In a particular embodiment, the kit is an antibody-based kit. Such a kit can comprise, for example, (1) a first antibody (e.g., attached to a solid support)) that binds to an EDG5 protein having an alanine at position 286, and, optionally, (2) a second, different antibody that binds to an EDG5 protein having an alanine at position 286, or to the first antibody and is conjugated to a detectable agent. If the second antibody is not present, then either the first antibody can be detectably labeled, or alternatively, another molecule that binds the first antibody can be detectably labeled. In any event, a labeled binding moiety is included to serve as the detectable reporter molecule, as known in the art.

A kit of the present invention can also be an oligonucleotide-based kit that can be used to determine whether the biological sample comprises a nucleic acid molecule that encodes an EDG5 protein having an alanine at position 286. An oligonucleotide-based kit of the present invention can comprise, for example: (1) an oligonucleotide, e.g., a detectably-labeled oligonucleotide, that hybridizes to a nucleic acid sequence that encodes an EDG5 protein having an alanine at position 286, or (2) a pair of primers useful for amplifying a nucleic acid molecule that encodes an EDG5 protein having an alanine residue at position 286.

Naturally, a kit of the present invention can comprise, e.g., a buffering agent, a preservative or a protein stabilizing agent. The kit also can comprise components necessary for detecting the detectable agent (e.g., an enzyme or a substrate).

Furthermore, the kit may also contain a control sample or series of control samples that can be assayed and compared to the test sample. Each component of the kit is usually enclosed within an individual container, and all of the various containers are within a single package. Instructions for observing whether the tested subject is suffering from or is at risk of type II Diabetes mellitus, venous thrombosis, or pulmonary embolism may also be enclosed.

Optionally, a kit of the present invention can also comprise directions for using the kit.

The identification of the polymorphism in the nucleotide sequence of EDG5 leading to the amino acid exchange at position 286 from Val to Ala in the EDG5 protein can be used to predict increased or normal risk for type II Diabetes mellitus and/or venous thrombosis/pulmonary embolism. It can be used e. g. in
1) methods based on sequencing the nucleotide region of interest (e.g. pyrosequencing, sequencing methods using radio-labeled nucleotides, or nucleotides which are labeled with a fluorescent dye, analysis of sequence fragments with mass spectrometry);
2) methods based on the hybridization of nucleotide sequences to the region of interest (e.g. DNA microarrays);
3) methods based on analyzing amplification products of the nucleotide region of interest (e.g. TaqMan analysis).

The identification of the polymorphism in the protein sequence of EDG5 comprising the amino acid exchange at position 286 from Val to Ala in the EDG5 protein can be used to predict increased or normal risk for type II Diabetes mellitus and/or venous thrombosis/pulmonary embolism. It can be used, e.g. in
1) methods based on sequencing the protein region of interest (e.g. standard protein degradation, analysis of protein sequence fragments with mass spectrometry);
2) methods based on using anti-EDG5 antibodies against the region of interest (e.g. ELISA);
3) methods based on analyzing functional activity of EDG5 in in-vitro assays using e. g. human, animal, bacterial, or yeast cells.

The detection of genetic polymorphisms in the EDG5 gene, in particular EDG5-286-VA (EDG5 variants having Alanine at position 286 in the protein as a consequence of pholymorphisms at the corresponding position on one allele of the EDG5 gene), and the resulting protein by analyzing human DNA or EDG5 protein may be used (a) as genetic markers for preventive treatments to type II Diabetes mellitus and/or venous thrombosis/pulmonary embolism, (b) as a genetic marker for adaptation of drug dose, (c) as a genetic marker for drug screening set-up adaptation and (d) as a genetic marker for patient selection in phase/clinical studies.

The identification of the polymorphism in the nucleotide sequence of the EDG5 gene leading to the amino acid exchange at position 286 from Val to Ala in the EDG5 protein can be used to predict increased or normal risk type II Diabetes mellitus and/or venous thrombosis/pulmonary embolism. It can be used e. g. in
1) methods based on sequencing the nucleotide region of interest (e.g. pyrosequencing, sequencing methods using radio-labeled nucleotides, or nucleotides which are labeled with a fluorescent dye, analysis of sequence fragments with mass spectrometry);
2) methods based on the hybridization of nucleotide sequences to the region of interest (e.g. DNA microarrays);
3) methods based on analyzing amplification products of the nucleotide region of interest (e.g. TaqMan analysis).

The identification of the polymorphism in the protein sequence of EDG5 comprising the amino acid exchange at position 286 from Val to Ala can be used to predict increased or normal risk for type II Diabetes mellitus and/or venous thrombosis/pulmonary embolism. It can be used, e.g. in
1) methods based on sequencing the protein region of interest (e.g. standard protein degradation, analysis of protein sequence fragments with mass spectrometry);
2) methods based on using anti-EDG5 antibodies against the region of interest (e.g. ELISA);
3) methods based on analyzing functional activity of EDG5 in in-vitro assays using e. g. human, animal, bacterial, or yeast cells.

The detection of genetic polymorphisms in the EDG5 gene, in particular EDG5-286-VA (EDG5 variants having Alanine at position 286 of the protein as a consequence of pholymorphisms at the corresponding position on one allele of the EDG5 gene), and the resulting protein by analyzing human DNA and EDG5 protein may be used (a) as genetic markers for preventive treatments to prevent type II Diabetes mellitus and/or venous thrombosis/pulmonary embolism, (b) as a genetic marker for adaptation of drug dose, (c) as a genetic marker for drug screening set-up adaptation and (d) as a genetic marker for patient selection in phase/clinical studies.

The present invention may be better understood by reference to the following non-limiting Examples, which are provided as exemplary of the invention. The following Examples are presented in order to more fully illustrate the preferred embodiments of the invention. They should in no way be construed, however, as limiting the broad scope of the invention.

EXAMPLES

The known EDG5 polymorphism at the position 286 of the EDG5 protein (NCBI accession number for protein sequence: NP_004221 (Table 1A); NCBI accession number for nucleotide sequence: AF034780 (Table 1 B)) was analyzed in a patient cohort with or without cardiovascular events or endpoints.

Example 1

Study Subjects (Study Population)

The genomic DNA of 1140 patients was screened for single nucleotide polymorphisms (SNPs) in the EDG5 gene leading to the protein variants EDG5-V286A. The phenotype of this patient cohort has been described previously (Winkelmann et al. (2001) Pharmacogenomics, 2, 1-73). Inclusion criteria have been: Caucasian individual of German ancestry, stable clinical condition (except for acute coronary syndrome [ACS]) and coronary angiogram. Exclusion criteria have been: acute illness other than ACS, chronic non-cardiac disease (i.e. rheumatic arthritis) and history of malignant disease within the previous five years. Basic characteristics of this patient cohort are outlined in Table 2.

Example 2

SNP Detection by Sequencing and Analysis

Example 2.1

Amplification of Genomic Region with Polymorphism of Interest

Amplification Primers:
1. For the detection of nucleotide exchange of valine to alanine at position 286 of the EDG5 gene sequence, the following primers were used:
   Forward primer: 5'-TCCACTGTCCTGCCTCTCTAC-3' (SEQ ID NO. 1)
   Reverse primer: 5'-TCTCCATGAACCCCTCTGCC-3' (SQE ID NO. 2)

PCR Protocol for Amplification:
All reagents are from Applied Biosystems (Foster City, USA): 20 ng of genomic DNA; 1 unit of TaqGold polymerase; 1× Taq polymerase buffer; 500 µM of dNTP; 2.5 mM of MgCl2; 200 nM of each amplification primer pair (for sequence see Amplification primer pair 1. above); H$_2$O ad 5 µl.

Amplification Program for PCR/Genotyping:

| | |
|---|---|
| 95° C. × 10 min | ×1 cycle |
| 95° C. × 30 sec | |
| 70° C. × 30 sec | ×2 cycles; |
| 95° C. × 30 sec | |
| 65° C. × 30 sec | ×2 cycles; |
| 95° C. × 30 sec | |
| 60° C. × 30 sec | ×2 cycles; |
| 95° C. × 30 sec | |
| 56° C. × 30 sec | |
| 72° C. × 30 sec | ×40 cycles; |
| 72° C. × 10 min | |
| 4° C. × 30 sec | ×1 cycle; |

Example 2.2

Identification of Polymorphisms of Interest

Protocol for Minisequencing and Detection of Polymorphisms:

All reagents are from Applied Biosystems (Foster City, USA). 2 µl of purified PCR product; 1.5 µl BigDye terminator kit; 200 nM of one sequencing primer (for sequence see forward or reverse Amplification primer 1. above); H2O ad 10 µl.

Amplification Program for Sequencing:

| | |
|---|---|
| 96° C. × 2' | ×1 cycle; |
| 96° C. × 10" | |
| 55° C. × 10" | |
| 65° C. × 4' | ×30 cycles; |
| 72° C. × 7' | |
| 4° C. × 30" | ×1 cycle; |

Analysis of Sequencing Products:

Sequences were analyzed first with sequencing analysis (Applied Biosystems, Foster City, USA) for raw data extraction, then processed with PHRED (base caller), PHRAP (assembler), POLYPHRED (SNP caller) and CONSED (results viewer). PHRED, PHRAP, POLYPHRED and CONSED are software designed at Washington University by Phil Green (http://www.genome.washington.edu).

Example 2.3

Statistical Approaches for Genotype/Phenotype Correlation

All analyses were done with SAS statistical package (Version 6.12, SAS Institute GmbH, Heidelberg/Germany). For the detection of associations between genetic polymorphisms and a large number of clinical relevant parameters, descriptive statistics were computed (median, quartiles) and Wilcoxon-rank-sum-tests were performed. Wilcoxon-rank-sum-test is used for the comparison of two independent samples. The computation of the test statistic is based on ranks in the pooled sample.

The search for associations between the SNPs and risk factors and diseases was done in a similar way. The Chi-Square-Test was performed and numbers and percentages were calculated to describe the data. The Chi-Square-Test is a statistical test for calculating the dependence of two variables. The values of the variables are contained in two or more classes. To analyze the association of those variables, a contingency table is used. This table contains as many rows as the number of realizations of the first variable and as many columns as the number of realizations of the second variable. Every cell contains a special patient's characteristic. To construct a test statistic, the differences of calculated and observed frequencies are computed.

After inspecting the results, relevant variables were selected. To take account of confounding co-variables, logistic regression was used to validate the results. The logistic regression method is used to analyze the influence of several explanatory variables on a certain response variable. The associated statistical test gives a p-value. The interpretation of this p-value is that there is a significant influence of the associated explanatory variable.

For a binary variable, the odds ratio has been calculated. The odds ratio is the ratio of the odds that an event will occur in one group to the odds that the event will occur in the other group.

Example 2.4

Analyses

The following abbreviations are used:

EDG5-286-VV defines the group of individuals, in which both of the EDG5 alleles code for a EDG5 gene variant leading to Valine (V) at position 286 of the EDG5 protein, this group is homozygous for this EDG5 polymorphism at position 286 of the EDG5 protein.

EDG5-286-VA defines the group of individuals, in which one of the EDG5 alleles codes for a EDG5 gene variant leading to Valine (V) at position 286 of the EDG5 protein and the other EDG5 allele codes for a EDG5 gene variant leading to Alanine (A) at position 286 of the EDG5 protein, this group is heterozygous for EDG5 polymorphism at position 286 of the EDG5 protein.

EDG5-286-AA defines the group of individuals, in which both of the EDG5 alleles code for a EDG5 gene variant leading to Alanine (A) at position 286 of the EDG5 protein, this group is homozygous for this EDG5 polymorphism at position 286 of the EDG5 protein.

The distribution of EDG5-286 variants in 1140 individuals is shown in Table 3. The EDG5-286-AA variant does not appear at all in this patient cohort. 2.1% of all patients are carriers of the EDG5-286-VA variant and 97.8% of the patients are carriers of the EDG5-286-VV variant.

Patients carrying EDG5-286-VA show an increased association for type II diabetes mellitus (DM Type II) and venous thrombosis/pulmonary embolism (VT/PE) compared to EDG5-286-VV patients. Statistical significance calculated with Chi-square test of the observed association is p-value=0.001 for the association with DM Type II and p-value=0.026 for the association with VT/PE (Tables 4A and 5A). Logistic regression models for analyzing the influence of confounding factors, such as myocardial infarction and hypertension resulted in a p-value=0.0022 for the association of EDG5-286-VA with DM Type II to p-value and p-value=0.0315 for the association of EDG5-286-VA with VT/PE (Tables 4B and 5B).

The odds ratios of decreased risk for DM Type II is 3.801 and for VT/PE 3.095 in individuals carrying the EDG5-286-VA variants compared to individuals with EDG5-286-VV variants (Tables 4C and 5C).

The EDG5-286-VA allele represents therefore a strong genetic marker to estimate decreased risk of DM Type II and venous thrombosis/pulmonary embolism.

Table 1:

Protein sequence of EDG5 (ENDOTHELIAL DIFFERENTIATION GENE 5). The protein sequence accession number (NCBI protein database) of EDG5 is NP_004221 (A), the nucleotide sequence accession number (NCBI nucleotide database) is AF034780 (B) and the accession number for EDG5 information in OMIM (ONLINE MENDELIAN INHERITANCE IN MAN) is 605111.

TABLE 1A

Protein Sequence of EDG5

(SEQ ID NO. 3)

```
  1 MGSLYSEYLN PNKVQEHYNY TKETLETQET TSRQVASAFI VILCCAIVVE NLLVLIAVAR

61 NSKFHSAMYL FLGNLAASDL LAGVAFVANT LLSGSVTLRL TPVQWFAREG SASITLSASV

121 FSLLAIAIER HVAIAKVKLY GSDKSCRMLL LIGASWLISL VLGGLPILGW NCLGHLEACS

181 TVLPLYAKHY VLCVVTIFSI ILLAIVALYV RIYCVVRSSH ADMAAPQTLALLKTVTIVLG

241 VFIVCWLPAF SILLLDYACP VHSCPILYKA HYFFAVSTLN SLLNPVIYTWRSRDLRREVL

301 RPLQCWRPGV GVQGRRRVGT PGHHLLPLRS SSSLERGMHM PTSPTFLEGN TVV
```

TABLE 1B

Nucleotide Sequence of EDG5

(SEQ ID NO. 4)

```
   1 ATGGGCAGCT TGTACTCGGA GTACCTGAAC CCCAACAAGG TCCAGGAACA CTATAATTAT

61 ACCAAGGAGA CGCTGGAAAC GCAGGAGACG ACCTCCCGCC AGGTGGCCTC GGCCTTCATC

121 GTCATCCTCT GTTGCGCCAT TGTGGTGGAA AACCTTCTGG TGCTCATTGC GGTGGCCCGA

181 AACAGCAAGT TCCACTCGGC AATGTACCTG TTTCTGGGCA ACCTGGCCGC CTCCGATCTA

241 CTGGCAGGCG TGGCCTTCGT AGCCAATACC TTGCTCTCTG GCTCTGTCAC GCTGAGGCTG

301 ACGCCTGTGC AGTGGTTTGC CCGGGAGGGC TCTGCCTCCA TCACGCTCTC GGCCTCTGTC

361 TTCAGCCTCC TGGCCATCGC CATTGAGCGC CACGTGGCCA TTGCCAAGGT CAAGCTGTAT

421 GGCAGCGACA AGAGCTGCCG CATGCTTCTG CTCATCGGGG CCTCGTGGCT CATCTCGCTG

481 GTCCTCGGTG GCCTGCCCAT CCTTGGCTGG AACTGCCTGG GCCACCTCGA GGCCTGCTCC

541 ACTGTCCTGC CTCTCTACGC CAAGCATTAT GTGCTGTGCG TGGTGACCAT CTTCTCCATC

601 ATCCTGTTGG CCATCGTGGC CCTGTACGTG CGCATCTACT GCGTGGTCCG CTCAAGCCAC

661 GCTGACATGG CCGCCCCGCA GACGCTAGCC CTGCTCAAGA CGGTCACCAT CGTGCTAGGC

721 GTCTTTATCG TCTGCTGGCT GCCCGCCTTC AGCATCCTCC TTCTGGACTA TGCCTGTCCC

781 GTCCACTCCT GCCCGATCCT CTACAAAGCC CACTACTTTT TCGCCGTCTC CACCCTGAAT

841 TCCCTGCTCA ACCCCGTCAT CTACACGTGG CGCAGCCGGG ACCTGCGGCG GGAGGTGCTT

901 CGGCCGCTGC AGTGCTGGCG GCCGGGGGTG GGGGTGCAAG GACGGAGGCG GGTCGGGACC

961 CCGGGCCACC ACCTCCTGCC ACTCCGCAGC TCCAGCTCCC TGGAGAGGGG CATGCACATG

1021 CCCACGTCAC CCACGTTTCT GGAGGGCAAC ACGGTGGTCT GA
```

TABLE 2

Basic characteristics of the patient cohort.

| | | n | % |
|---|---|---|---|
| Total | | 1140 | |
| Gender | Female | 782 | 68.6 |
| | Male | 358 | 31.4 |
| Age* | | 63.3 | |
| | | (56.5-70.9) | |
| BMI* | | 27.9 | |
| (Body Mass Index) | | (25.0-30.3) | |
| Hypertension | | 670 | 58.8 |
| Smoker | | 731 | 64.1 |
| Diabetes | no oGT | 279 | 24.5 |
| | normal GT | 264 | 23.2 |
| | impaired GT | 236 | 20.7 |
| | diabetes new | 169 | 14.8 |
| | known diabetes | 192 | 16.8 |
| Diabetes | diabetes (total) | 361 | 31.7 |
| | no diabetes (total) | 779 | 68.3 |
| Stable CAD | CCS 1 | 457 | 40.1 |
| | CCS 2 | 409 | 35.9 |
| | CCS 3 | 191 | 16.8 |
| | CCS 4 | 83 | 7.3 |
| Unstable CAD | no ACS (noCAD/stable CAD/MI > 15 d) | 743 | 65.2 |
| | tropT – UA (no acute MI) | 250 | 21.9 |
| | tropT + UA (no clinical MI) | 42 | 3.7 |
| | post acute MI (1-15 d) | 105 | 9.2 |

*Median and Quartiles (Q1-Q3)

TABLE 3

Distribution of EDG5 variants in the analyzed patient cohort.

| | Number of patients (%) |
|---|---|
| EDG5-286-VV | 1116 (97.9%) |
| EDG5-286-VA | 24 (2.1%) |
| EDG5-286-AA | 0 (0%) |

TABLE 4A

Association of EDG5-286 variants with type II diabetes mellitus calculated by Chi-square test. An increased frequency of EDG5-286-VA carriers in the type II diabetes mellitus positive group could be observed compared to EDG5-286-VV patients.

| | Type II Diabetes Mellitus | | |
|---|---|---|---|
| | Number of patients without T-II-DM (%) | Number of patients with T-II-DM (%) | p-value |
| EDG5-286-VA | 9 (37.5%) | 15 (62.5%) | 0.001 |
| EDG5-286-VV | 770 (69.0%) | 346 (31.0%) | |

TABLE 4B

Calculation of statistical significance for EDG5-286-VA association with type II diabetes mellitus by logistic regression.

| | p-value (logistic regression) |
|---|---|
| EDG5-286-VA | 0.0022 |
| Male gender | 0.9926 |
| Smoker | 0.7159 |
| Arterial hypertension | 0.0001 |
| MI | 0.0044 |
| ACS | 0.5657 |
| Tot. Cholesterol >= 240 or drug history | 0.4831 |

TABLE 4B-continued

Calculation of statistical significance for EDG5-286-VA association with type II diabetes mellitus by logistic regression.

| | p-value (logistic regression) |
|---|---|
| Venous thrombosis/pulmonary embolism | 0.5843 |

TABLE 4C

Calculation of odds ratios for the risk of having type II diabetes mellitus of EDG5-286-VA patients compared to EDG5-286-VV patients.

| | | 95%-confidence interval | | |
|---|---|---|---|---|
| | odds ratio | lower | Upper | p-value |
| Type II Diabetes Mellitus | 3.801 | 1.614 | 8.949 | 0.0022 |

TABLE 5A

Association of EDG5-286 variants with venous thrombosis/pulmonary embolism calculated by Chi-square test. An increased frequency of EDG5-286-VA carriers in the venous thrombosis/pulmonary embolism positive group could be observed compared to EDG5-286-VV patients.

| | Venous thrombosis/pulmonary embolism (VT/PE) | | |
|---|---|---|---|
| | Number of patients without VT/PE (%) | Number of patients with VT/PE (%) | p-value |
| EDG5-286-VA | 19 (79.2%) | 5 (20.8%) | 0.026 |
| EDG5-286-VV | 1030 (93.0%) | 78 (7.0%) | |

TABLE 5B

Calculation of statistical significance for EDG5-286-VA association venous thrombosis/pulmonary embolism (VT/PE) by logistic regression.

| | p-value (logistic regression) |
|---|---|
| EDG5-286-VA | 0.0351 |
| Male gender | 0.0004 |
| Smoker | 0.0965 |
| Arterial hypertension | 0.7338 |
| MI | 0.8597 |
| ACS | 0.9270 |
| Diabetes mellitus type II | 0.5796 |
| Tot. Cholesterol >= 240 or drug history | 0.9452 |

TABLE 5C

Calculation of odds ratios for the risk of having venous thrombosis/pulmonary embolism of EDG5-286-VA patients compared to EDG5-286-VV patients.

| | | 95%-confidence interval | | |
|---|---|---|---|---|
| | odds ratio | lower | Upper | p-value |
| Venous thrombosis/Pulmonary embolism | 3.095 | 1.082 | 8.853 | 0.0351 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for identifying an increase in risk for type II diabetes mellitus, venous thrombosis, pulmonary embolism or a combination thereof in a subject, comprising the steps of:
   (a) removing a biological sample from the subject that comprises a human EDG5 protein;
   (b) determining whether an amino acid residue exchange of valine to alanine at position 286 of the human EDG5 protein of SEQ ID NO: 3 is present in the protein from the biological sample, wherein the presence of alanine at this position is correlated with an increased risk for type II diabetes mellitus, venous thrombosis, pulmonary embolism or a combination thereof in said subject.

* * * * *